United States Patent [19]

Röchling

[11] Patent Number: 5,198,431
[45] Date of Patent: Mar. 30, 1993

[54] CONCENTRATED AQUEOUS EMULSIONS OF NEOPHANES AND AZANEOPHANES FOR USE IN PLANT PROTECTION

[75] Inventor: Hans Röchling, Bad Soden Im Taunus, Fed. Rep. of Germany

[73] Assignee: Hoechst Aktiengesellschaft, Frankfurt am Main, Fed. Rep. of Germany

[21] Appl. No.: 656,409

[22] Filed: Feb. 15, 1991

[30] Foreign Application Priority Data

Feb. 17, 1990 [DE] Fed. Rep. of Germany ....... 4005155

[51] Int. Cl.$^5$ .................... A01N 55/00; A61K 31/695
[52] U.S. Cl. ...................................... 514/63; 514/937; 514/941
[58] Field of Search ............................ 514/63, 941, 937

[56] References Cited

U.S. PATENT DOCUMENTS

| | | | |
|---|---|---|---|
| 2,547,724 | 4/1951 | Sundholm | 514/442 |
| 3,639,262 | 2/1972 | Milligan | 514/491 |
| 4,775,664 | 10/1988 | Schubert et al. | 514/63 |
| 4,804,653 | 2/1989 | Strunk et al. | 514/63 |
| 4,864,027 | 9/1989 | Schubert et al. | 546/14 |
| 4,966,902 | 10/1990 | Schubert et al. | 514/277 |

FOREIGN PATENT DOCUMENTS

| | | |
|---|---|---|
| 62453 | 10/1982 | European Pat. Off. |
| 202893 | 11/1986 | European Pat. Off. |
| 257533 | 3/1988 | European Pat. Off. |
| 296857 | 12/1988 | European Pat. Off. |
| 336199 | 10/1989 | European Pat. Off. |
| 3604781 | 8/1987 | Fed. Rep. of Germany. |

Primary Examiner—Allen J. Robinson
Assistant Examiner—B. Bembenick
Attorney, Agent, or Firm—Curtis, Morris & Safford

[57] ABSTRACT

Concentrated aqueous emulsions of compounds of the formula I

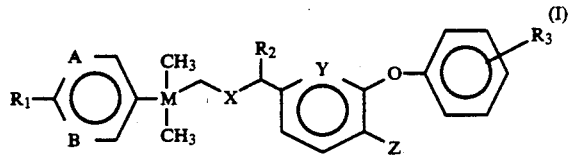

in which
A and B independently of one another are CH, $CR_4$ or N,
X is $CH_2$, O or S,
Y is CH or N,
Z is H or F,
$R_1$ and $R_4$ independently of one another are H, halogen, $(C_1-C_3)$-alkyl, $(C_1-C_3)$-haloalkyl, $(C_1-C_3)$-alkoxy, $(C_1-C_3)$-haloalkoxy, $(C_1-C_3)$-alkylthio or $(C_1-C_4)$-haloalkylthio, or $R_1$ and $R_4$ together are $-CH_2-O-CH_2-$;
$R_2$ is H, $(C_1-C_3)$-alkyl, ethynyl, vinyl, halogen or cyano,
$R_3$ is H, halogen, $(C_1-C_4)$-alkyl or $(C_1-C_3)$-alkoxy and
M is C or Si, which contain a combination of an anionic emulsifier, an n-butanol/propylene oxide/ethylene oxide block oxalkylate and a sodium magnesium (and/or aluminum) silicate having a layered structure, have very good storage stability, good pourability and advantageous properties in use.

7 Claims, No Drawings

CONCENTRATED AQUEOUS EMULSIONS OF NEOPHANES AND AZANEOPHANES FOR USE IN PLANT PROTECTION

The present invention relates to concentrated aqueous emulsions of compound of the formula I

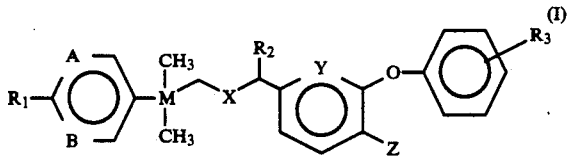

in which
A and B independently of one another are CH, CR$_4$ or N,
X is CH$_2$, O or S,
Y is CH or N,
Z is H or F,
R$_1$ and R$_4$ independently of one another are H, halogen, (C$_1$–C$_3$)-alkyl, (C$_1$–C$_3$)-haloalkyl, (C$_1$–C$_3$)-alkoxy, (C$_1$–C$_3$)-haloalkoxy, (C$_1$–C$_4$)-alkylthio or (C$_1$–C$_4$)-haloalkylthio, or R$_1$ and R$_4$ together are —CH$_2$—O—CH$_2$—;
R$_2$ is H, (C$_1$–C$_3$)-alkyl, ethynyl, vinyl, halogen or cyano,
R$_3$ is H, halogen, (C$_1$–C$_4$)-alkyl or (C$_1$–C$_3$)-alkoxy and
M is C or Si, which contain a combination of an anionic emulsifier, an n-butanol/propylene oxide/ethylene oxide block oxalkylate and a sodium magnesium (and/or aluminum) silicate having a layered structure.

Alkyl represents a straight-chain or branched alkyl radical.

Preferably, A and B are CH or N, X is CH$_2$, R$_1$ is (C$_1$–C$_3$)-alkoxy, R$_2$ is H, R$_3$ is H or F and M is Si.

Particularly preferred amongst the compounds of the formula I is that in which M is Si, R$_1$ is ethoxy, A and B are CH, X is CH$_2$, R$_2$ is H, Y is CH, Z is F and R$_3$ is H (Ia).

Active substances from the group of the neophanes and azaneophanes (I) are suitable for controlling animal pests, in particular insects, arachnids and nematodes which occur in agriculture, in forests, in the protection of stored goods and materials, and in the hygiene field, while having good plant compatibility and favorable toxicity toward warm-blooded species. They are resistant against normally-sensitive and resistant species and against all or some stages of development (EP-A 0,224,024, EP-A 0,249,015, EP-A 0,288,810). These documents also describe the customary formulation types for insecticides or acaricides.

In addition to a broad insecticidal activity, the neophanes and azaneophanes of the formula I have an unusually favorable toxicity toward warm-blooded species and very low toxicity toward fish and birds. It was intended to support these positive properties of the active substances by a suitable formulation. A first idea was to formulate the compounds I, which are present in the form of oily and readily-soluble liquids, as emulsifiable concentrates (EC).

However, when an emulsifiable concentrate is prepared, it is necessary to employ solvents whose use entails a series of disadvantages. In contrast, concentrated aqueous emulsions which can be prepared without solvents have the following advantages compared with an EC:
high, or no, flash point, hence safer during transport and storage;
safer for the user since less toxic to skin and mucous membranes;
more ecological, little or no offensive odor.

It was therefore an object to develop concentrated aqueous emulsions of neophanes and azaneophanes (I) which have sufficient storage stability, good pourability and good properties in use.

The preparation of concentrated aqueous emulsions (EW) is described in principle in German Offenlegungsschrift 3,009,944, German Offenlegungsschrift 3,235,612, EP-A 0,107,023, EP-A 0,160,182 and EP-A 0,297,207. However, the processes described in these publications cannot be used advantageously for the active substances (I) to be formulated in this case since they lead to formulations which have insufficient storage stability or which are too viscous.

Generally suitable for the preparation of concentrated aqueous emulsions are phosphorylated surfactants, for example phosphorylated ethylene oxide/propylene oxide block polymers and ethoxylated and phosphorylated styryl-substituted phenols. Use of these emulsifiers, also in combination with various, non-phosphorylated surfactants as are described in German Offenlegungsschrift 3,346,637, German Offenlegungsschrift 3,304,677 and EP-A 0,257,286, was not successful in the case of the compounds I: at storage temperatures between 0° C. and 25° C., phase separation occurs. If, to prevent this phase separation, the percentage of emulsifiers is increased, then viscosity increases dramatically, which results in poor pourability and, in some cases, also leads to waxy solidification when stored under warm conditions.

Surprisingly, it has now been found that the compounds of the formula I can be formulated to give aqueous emulsions which are storage-stable and have good pourability (suitable viscosity) over a large temperature range when a combination of an anionic emulsifier, an n-butanol/-propylene oxide/ethylene oxide block oxalkylate and a sodium magnesium (and/or aluminum) layered silicate are used. Moreover, the aqueous emulsions according to the invention have the abovementioned ecological and user-friendly properties. The total amount of emulsifiers can be kept extraordinarily low and use of solvents is not required, so that the formulation contains few ecotoxic substances.

The following can be used as anionic emulsifiers: salts of dodecylbenzenesulfonic acid, salts of optionally chlorinated (C$_{13}$–C$_{18}$)-alkanesulfonic acids, furthermore emulsifiers from the group comprising the (C$_{10}$–C$_{16}$)-alkyl-mono- to hexaglycol ether sulfate salts and of the α(C$_{14}$–C$_{19}$)-alkenol sulfate salts. In particular, it is favorable to employ the salts of dodecylbenzenesulfonic acid. The term salts represents alkali metal salts, alkaline earth metal salts or ammonium salts, preferably Na salts or Ca salts. Particularly preferred is the Ca salt of dodecylbenzenesulfonic acid (Ca phenylsulfonate, manufactured by Hoechst AG).

The n-butanol/propylene oxide/ethylene oxide block oxalkylate can consist to 1–3% by weight of n-butanol, to 40–50% by weight of propylene oxide and to 50–60% by weight of ethylene oxide. It preferably consists of 2% by weight of n-butanol, 44% by weight of propylene oxide and 54% by weight of ethylene oxide (HOE S 3510, manufactured by Hoechst AG).

The layered silicate used can be a sodium magnesium silicate, a sodium aluminum silicate, or a foam in which the two silicates are mixed.

The layered silicates can be of natural origin or are derived from a synthetic preparation. The sodium ion can be replaced partly by lithium. A sodium magnesium silicate of synthetic origin, for example ®Laponite RD (Laporte-Ind. Ltd., Great Britain), is preferred. The abovementioned layered silicates are described, for example, in Ullmanns Encyklopädie der technischen Chemie [Ullmann's Encyclopedia of Industrial Chemistry], 4th edition, Volume 21, p. 370.

The amount of emulsifier mixture in the finished formulation is preferably 4–17% by weight, in particular 5–14% by weight. The aqueous emulsions according to the invention contain 1.5–7% by weight, preferably 1.9–5% by weight, of the anionic emulsifier. The amount of the non-ionic emulsifier (block oxalkylate) is 2.5–10% by weight, in particular 3.1–9% by weight. The sodium magnesium (and/or aluminum) layered silicate to be used according to the invention is present in the finished formulation in amounts of 0.1–1.5% by weight, preferably 0.2–0.8% by weight, this formulation containing 0.5–80% by weight, in particular 10–50% by weight, of the active substances of the formula I.

Mixtures of several representatives of the three types of emulsifier mentioned also fulfil the purpose according to the invention.

If hard water is used, it is advantageous to add complexants, for example sodium polyphosphate of an average chain length having a total $P_2O_5$ content of about 60%, or sodium tripolyphosphate, in amounts of 0.05 to 2% by weight.

In addition, the formulations according to the invention can also contain further customary formulation auxiliaries. For example, as antifreeze agents: monovalent or polyvalent alcohols, glycol ethers or urea, in particular glycerol, isopropanol, propylene glycol monomethyl ether, dipropylene glycol monomethyl ether or tripropylene glycol monomethyl ether, or cyclohexanol. The amount of these antifreeze agents is between 0.2 and 20% by weight.

All the formulation auxiliaries mentioned are substances sufficiently known to those skilled in the art and are described in the literature (cf. Winnacker-Küchler, "Chemische Technologie" [Chemical Technology]", Volume 7, C. Hauser Verlag Munich, 4th edition 1986; McCutcheon's "Detergents and Emulsifiers Annual" MC Publ. Corp., Ridgewood N.J.; Sisley and Wood "Encyclopedia of Surface Active Agents", Chem. Publ. Co. Inc., N.Y. 1964; Schönfeldt, "Grenzflächenaktive Äthylenoxidaddukte [Surface-active Ethylene Oxide Adducts]", Wiss. Verlagsgesell., Stuttgart 1976).

For the preparation of the formulations mentioned here, active substance and emulsifiers are first stirred at 25° to 45° C. until a solution has formed. 1 to 2 hours are generally required for this. An aqueous solution of the layered silicate and the polyphosphate is then prepared. This aqueous solution is then added dropwise to the active substance/emulsifier solution, and the mixture is then stirred for another 2 to 5 hours at 25° to 30° C. This gives emulsions of particle sizes of 50% <0.37–0.44 μm. The reverse procedure is also possible, by first introducing the aqueous solution of the layered silicate and the polyphosphate, and adding dropwise the organic solution of emulsifiers and active substance with stirring. The stirring times and temperatures are the same. This gives emulsions with particle sizes of 50% <0.35–0.40 μm.

The invention is illustrated by the preparation examples which follow:
the particle size was determined using a Malvern Master Sizer MS20 ® (manufactured by Malvern). Amount in the finished formulation I.
a)
40.0% by weight of a compound of the formula I
2.5% by weight of calcium dodecylbenzenesulfonate (Ca phenylsulfonate, Hoechst AG)
5.4% by weight of n-butanol/propylene oxide/ethylene oxide block oxalkylate (HOE S3510)
are stirred for 2 hours at 40° C. until a solution has formed.

b)
0.1% by weight of sodium polyphosphate of an average chain length having a $P_2O_5$ content of about 60%
0.4% by Weight of sodium magnesium layered silicate are then dissolved in 51.6% by weigth of water.
A stirring time of about 1 hour is required for this process.
The aqueous solution b) is now added dropwise to the organic phase a), with stirring.
After the dropwise addition, stirring is continued for 3 hours at 25°–30° C.
An emulsion having a particle size of 50% <0.38 μm is formed.

II.
a)
38.0% by weight of a compound of the formula I
2 2% by weight of calcium dodecylbenzenesulfonate
5.2% by weight of n-butanol/propylene oxide/ethylene oxide block oxalkylate
are stirred for 2 hours at 40° C. until a solution has formed. This organic phase is added dropwise with stirring to a solution of b)
0.1% by weight of sodium tripolyphosphate 0.3% by weight of sodium magnesium layered silicate in 54.2% by weight of water.
Stirring is then continued for 3 hours at 25°–30° C.
An emulsion having a particle size of 50% <0.36 μm is formed.

III.
a)
42.0% by weight of a compound of the formula I
2.8% by weight of calcium chloro-($C_{13}$–$C_{18}$)alkanesulfonate (1.2–1.6 Cl per mole of alkanesulfonate)
5.6% by weight of n-butanol/propylene oxide/ethylene oxide block oxalkylate
are stirred for 2 hours at 35°–40° C. until a solution has formed.

b)
0.1% by weight of sodium tripolyphosphate
0.4% by weight of sodium magnesium layered silicate are then dissolved in
49.1% by weight of water.
A stirring time of about 1 hour is required for this process.

The aqueous solution b) is now added dropwise to the organic phase a), with stirring.

After the dropwise addition, stirring is continued for 4 hours at 25°-30° C.

An emulsion having a particle size of 50% <0.41 μm is formed.

IV.
a)
20.0% by weight of a compound of the formula I
3.5% by weight of calcium dodecylbenzenesulfonate
8.5% by weight of n-butanol/propylene oxide/ethylene oxide block oxalkylate are stirred for 2.5 hours at 40° C. until a solution has formed.

b)
0.13% by weight of sodium tripolyphosphate
0.50% by weight of sodium magnesium layered silicate are then dissolved in
67.37% by weight of water.

A stirring time of about 1 hour is required for this process.

The aqueous solution b) is now added dropwise to the organic phase a), with stirring.

After the dropwise addition, stirring is continued for 3 hours at 25°-30° C.

An emulsion having a particle size of 50% <0.41 μm is formed.

The concentrated aqueous emulsions of Preparation Examples I-IV are homogenous after storage for 3 months at 20° C., 40° C. and 50° C., after storage for 14 days at 54° C. and after storage for 14 days at 0° C., no phase separation or precipitation of solids is observed.

Before and after storage, the concentrated aqueous emulsions of Examples I to IV meet the international test requirements when diluted to use concentration; i.e. an emulsion diluted with water at 30° C. and a hardness of 342 ppm (CIPAC standard water D[1]) to 5% shows no creamy or oily separation after a standing time of 6 hours.

[1] CIPAC-Handbook, Vol. 1, p. 878, Collaborative International Pesticides Analytical Council Ltd. (1970) s.a. Specifications for Pesticides used in public Health, World Health Organization, Geneva (1973).

The viscosity of the concentrated aqueous emulsions of Preparation Examples I to IV is 440-445 mPa×sec at a low shear stress of 16.8×sec$^{-1}$, and 110-115 mPa×sec at a higher shear stress of 144×sec$^{-1}$, measured using a Rheomat 115, manufactured by Contraves.

This guarantees good pourability of the formulations.

I claim:

1. A concentrated aqueous emulsion of a compound of the formula I

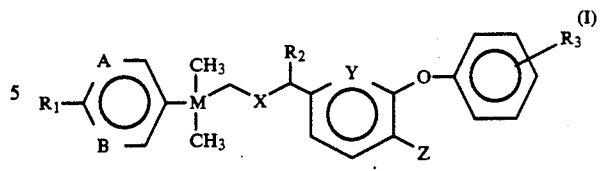

in which
A and B independently of one another are CH, CR$_4$ or n,
X is CH$_2$, O or S,
Y is CH or N,
Z is H or F,
R$_1$ and R$_4$ independently of one another are H, halogen, (C$_1$-C$_3$)-alkyl, (C$_1$-C$_3$)-haloalkyl, (C$_1$-C$_3$)-alkoxy, (C$_1$-C$_3$)-haloalkoxy, (C$_1$-C$_4$)-alkylthio or (C$_1$-C$_4$)-haoalkoxy, or R$_1$ and R$_4$ together are —CH$_2$—O—CH$_2$—;
R$_2$ is H, (C$_1$-C$_3$)-alkyl, ethynyl, vinyl, halogen or cyano,
R$_3$ is H, halogen, (C$_1$-C$_4$)-alkyl or (C$_1$-C$_3$)-alkoxy and
M is Si,
which contains a combination of 1.5-7% by weight of an anionic emulsifier selected from the group consisting of salts of dodecylbenzene sulfonic acid, salts of optionally chlorinated (C$_{13}$-C$_{18}$)-alkanesulfonic acids, (C$_{10}$-C$_{16}$)-alkylmono to hexaglycol ether sulfate salts and α-(C$_{13}$-C$_{19}$)-alkenosulfate salts, 2.5-10% by weight of an n-butanol/-propylene oxide/ethylene oxide block oxalkylate, 0.1-1.5% by weight of a sodium magnesium (and/or aluminum) silicate having a layered structure, and 0.5-80% by weight of the compound of formula I.

2. A concentrated aqueous emulsion as claimed in claim 1, in which, in formula I, A and B are CH or N, X is CH$_2$, R$_1$ is (C$_1$-C$_3$)-alkoxy, R$_2$ is H and R$_3$ is H or F.

3. A concentrated aqueous emulsion as claimed in claim 1, in which, in formula I, R$_1$ is ethoxy, A and B are CH, X is CH$_2$ and H, Y is CH, Z is F and R$_3$ is H.

4. A concentrated aqueous emulsion as claimed in claim 1, which contains 1.9-5% by weight of anionic emulsifier, 3.1-9% by weight of an n-butanol/-propylene oxide/ethylene oxide block oxalkylate and 0.2-0.8% by weight of a sodium magnesium (and/or aluminum) layered silicate.

5. A concentrated aqueous emulsion as claimed in claim 1, in which the n-butanol/propylene oxide/ethylene oxide block oxalkylate consists to 1-3% by weight of n-butanol, to 40-50% by weight of propylene oxide and to 50-60% by weight of ethylene oxide.

6. A concentrated aqueous emulsion as claimed in claim 1, in which an alkali metal salt or alkaline earth metal salt of dodecylbenzenesulfonic acid is used as the anionic emulsifier.

7. A method of controlling harmful insects or acarids, in which an effective amount of an aqueous emulsion as claimed in claim 1 is applied to these harmful insects or acarids or to plants, areas or substrates infested with them.

* * * * *